United States Patent

Nadelson

[11] 4,112,108
[45] * Sep. 5, 1978

[54] ISOXAZOLYL BENZAMIDES

[75] Inventor: Jeffrey Nadelson, Denville, N.J.

[73] Assignee: Sandoz, Inc., E. Hanover, N.J.

[*] Notice: The portion of the term of this patent subsequent to Oct. 19, 1993, has been disclaimed.

[21] Appl. No.: 747,772

[22] Filed: Dec. 6, 1976

[51] Int. Cl.² .................... C07D 261/08; A61K 31/42
[52] U.S. Cl. ................................ 424/272; 260/307 H
[58] Field of Search .................... 260/307 H; 424/272

[56] References Cited

U.S. PATENT DOCUMENTS

| | | | |
|---|---|---|---|
| 3,772,284 | 11/1973 | Singh et al. | 260/239 A |
| 3,987,179 | 10/1976 | Nadelson | 424/272 |
| 4,032,644 | 6/1977 | Nadelson | 424/272 |

Primary Examiner—Raymond V. Rush
Attorney, Agent, or Firm—Gerald D. Sharkin; Robert S. Honor; Timothy G. Rothwell

[57] ABSTRACT

This disclosure describes compounds of the formula

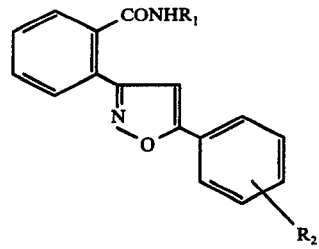

where
$R_1$ is straight chain alkyl, and
$R_2$ is hydrogen, halo having an atomic weight of about 19 to 36, lower alkoxy or trifluoromethyl, which are useful as minor tranquilizers and sleep inducers.

7 Claims, No Drawings

ISOXAZOLYL BENZAMIDES

This invention relates to isoxazolyl benzamides which exhibit minor tranquilizer and sleep-inducer activity. In particular, it relates to o-(5-substituted or unsubstituted phenyl-3-isoxazolyl)-N-alkylbenzamides, and intermediates thereof.

The compounds of this invention may be represented by the following structural formula

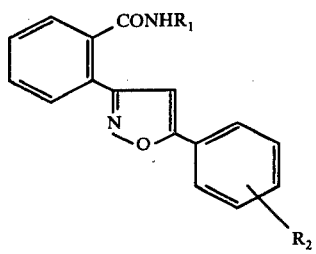

where
R$_1$ represents straight chain lower alkyl, i.e. straight chain lower alkyl having 1 to 4 carbon atoms, e.g., methyl, ethyl, propyl and the like, and
R$_2$ represents hydrogen, halo having an atomic weight of about 19 to 36, lower alkoxy, i.e., alkoxy having 1 to 4 carbon atoms, e.g., methoxy, ethoxy, isopropoxy and the like, or trifluoromethyl.

The compounds of formula (I) are prepared according to the following reaction scheme:

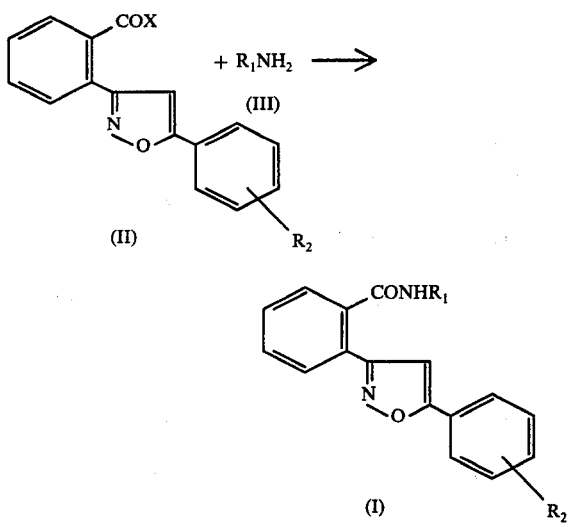

where X is chlorine or bromine, and R$_1$ and R$_2$ are as defined above.

The compounds of formula (I) are prepared by reacting a compound of the formula (II) in an inert organic solvent such as tetrahydrofuran, dioxane or diethylether, the latter being especially preferred, with a compound of the formula (III), optionally in the presence of an inert oganic solvent such as those illustrated above. It is preferred, however, that the compound of the formula (III) be employed in a concentrated aqueous solution that is greater than 30% by weight of a compound of the formula (III) in water. The temperature of the reaction is not critical, but it is preferred that the reaction be carried out at a temperature between about −20° to +25° C., preferably from about 0° to 10° C. The reaction may be run from 5 to 24 hours, preferably from about 18 to 20 hours. The product is recovered using conventional techniques, e.g., recrystallization.

The compounds of formula (II) are prepared according to the following reaction scheme:

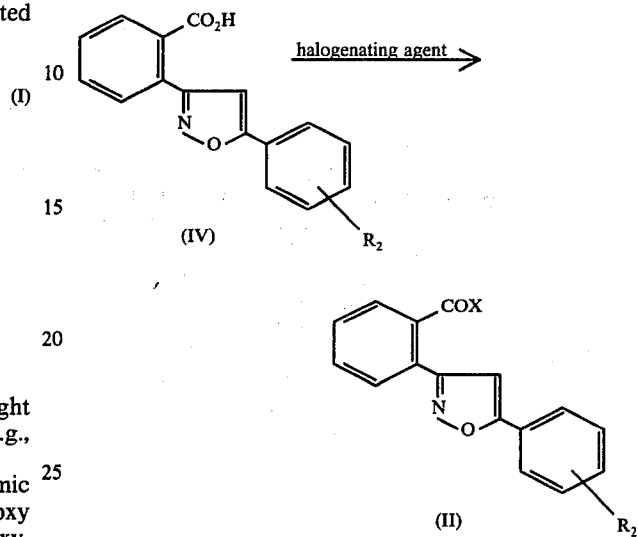

where X and R$_2$ are as defined above.

The compounds of formula (II) are prepared by reacting a compound of the formula (IV) with a halogenating agent optionally in the presence of an inert organic solvent. The preferred halogenating agents include thionyl chloride, thionyl bromide, phosphorous oxychloride, phosphorous pentachloride and the like, expecially thionyl chloride. Although an inert organic solvent such as an aromatic hydrocarbon, e.g., benzene, toluene, and the like or a halogenated hydrocarbon such as methylene dichloride and the like can be employed, it is preferred that the reaction be carried out in an excess of the halogenating agent employed, e.g., thionyl chloride. The temperature of the reaction is not critical, but it is preferred that the reaction be carried out at a temperature between about 50° to 120° C., preferably the reflux temperature of the solvent. The reaction may be run from 1 to 12 hours, preferably from about 3 to 6 hours. The product is recovered by conventional techniques, e.g., evaporation.

The compounds of formula (IV) are prepared according to the following reaction scheme:

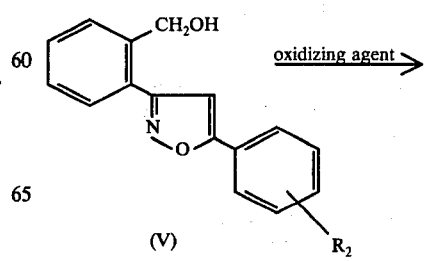

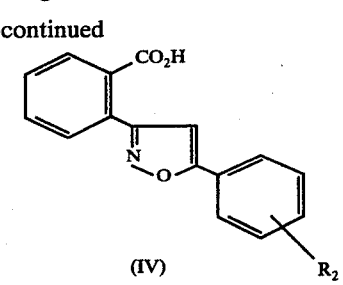

(IV)

where $R_2$ is as defined above.

The compounds of formula (IV) are prepared by reacting a compound of the formula (V) with an oxidizing agent such as chromium trioxide, potassium permanganate, and the like, preferably chromium trioxide under acid conditions in the presence of acetone and water. Although the particular acid employed is not critical, the preferred acids include the mineral acids such as hydrochloric acid, acetic acid or sulfuric acid, the latter being especially preferred. The particular solvent employed is preferably acetone in combination with water, although the combination of water and other inert water miscible solvents could also be employed such as the ethers, e.g., dioxane, tetrahydrofuran and the like. The temperature of the reaction is not critical, but it is preferred that the reaction be run from about 10° to 50° C., preferably from about 20° to 30° C. The reaction is run from about 1 to 6 hours, preferably from about 2.5 to 3.5 hours. The product is recovered using conventional techniques, e.g., trituration followed by filtration.

The compounds of formula (V) are prepared according to the following reaction scheme:

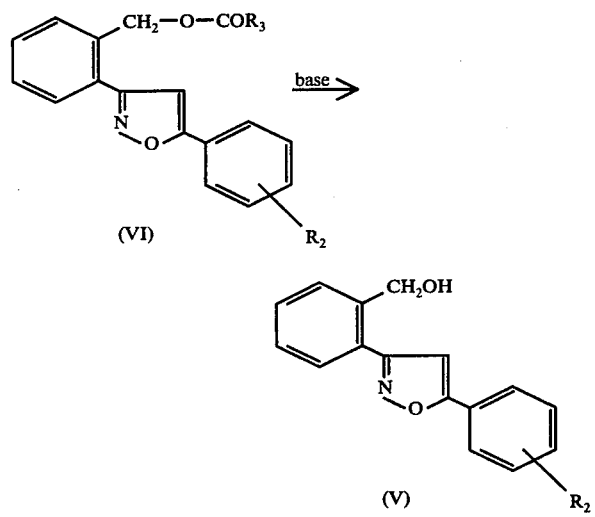

where
$R_3$ represents lower alkyl having 1 to 2 carbon atoms, and
$R_2$ is as defined above.

The compounds of formula (V) are prepared by reacting a compound of the formula (VI) with a strong inorganic base in the presence of an aqueous solvent. Although the particular inorganic base employed is not critical, the preferred bases include the alkali metal hydroxides, for example potassium hydroxide, sodium hydroxide, lithium hydroxide and the like, especially sodium hydroxide. The particular aqueous solvent employed is not critical, but it is preferred that the reaction be run in water, or any inert water miscible solvent including the lower alkanols, e.g., methanol, ethanol, and the like, acetone or dioxane, preferably ethanol. The temperature of the reaction is not critical, but it is preferred that the reaction be run at a temperature of from about 0° to 80° C., preferably from about 20° to 30° C. The reaction is run from about 2 to 6 days, preferably from about 3 to 5 days. The product is recovered using conventional techniques, e.g., crystallization.

The compounds of formula (VI) are prepared according to the following reaction scheme:

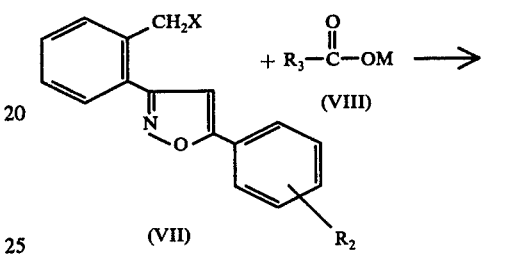

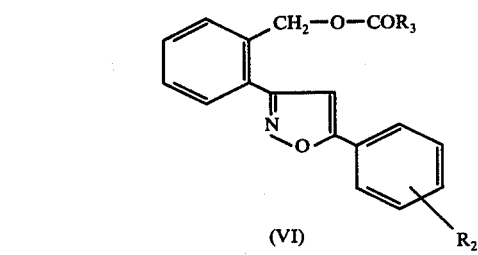

where M represents potassium or sodium, and X, $R_2$ and $R_3$ are as defined above.

The compounds of formula (VI) are prepared by reacting a compound of the formula (VII) with a compound of the formula (VIII) in the presence of an organic solvent. The preferred solvents include the organic acids which correspond to $R_3$—$CO_2H$, e.g., acetic acid or propionic acid, preferably acetic acid. The temperature of the reaction is not critical, but it is preferred that the reaction be run at a temperature of from about 50° to 150° C., preferably the reflux temperature of the solvent. The reaction is run from about 12 to 30 hours, preferably from about 21 to 23 hours. The product is recovered using conventional techniques, e.g., distillation followed by crystallization.

The compounds of formula (VII) are prepared according to the following reaction scheme:

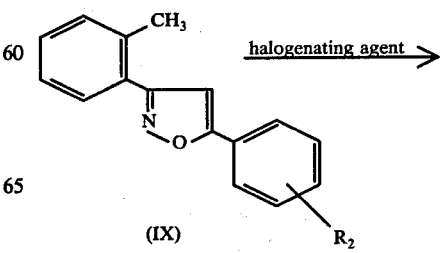

(IX)

-continued

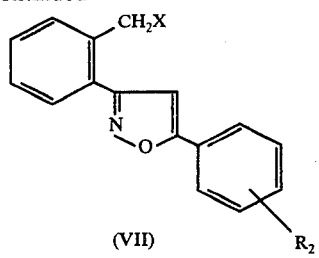

(VII)

where X and R₂ are as defined above.

The compounds of formula (VII) are prepared by treating a compound of the formula (IX) with a halogenating agent in the presence of an inert organic solvent and free radical initiator. The halogenating agent which can be used is bromine, chlorine, N-bromosuccinimide, N-chlorosuccimide, N-bromo-acetamide and the like. The particular agent used is not critical, but N-bromosuccinimide is preferred. In the preferred process, the free radical initiator used is an organic or inorganic peroxide, especially benzoyl peroxide. The reaction may also be carried out under artificial light. Although the particular solvent used is not critical, the preferred solvents include the halogenated hydrocarbons such as methylene dichloride, chloroform, carbon tetrachloride and the like, the aromatic hydrocarbons such as benzene, and the like, especially preferred is carbon tetrachloride. The temperature of the reaction is not critical, but reflux temperature of the solvent is preferred. The reaction is run from about 4 to 16 hours, preferably from about 5 to 7 hours. The product is recovered using conventional techniques, e.g., trituration.

Many of the compounds of formulae (III), (VIII) and (IX) are known and may be prepared by methods described in the literature. The compounds of formulae (III), (VIII) and (IX) not specifically described may be prepared by analogous methods from known starting materials.

The compounds of formula (I) are useful because they possess pharmacological activity in animals as sleep inducers and minor tranquilizers as indicated 1) by the hexobarbital reinduction method of Winter, J. Pharmacol. and Exp. Therap., 94, 7-11, 1948, in which the reinduction of anethesia is used to determine sedative-hypnotic activity in mice given 70 mg/kg. of animal body weight i.p. of hexobarbital followed immediately after the mice regain their righting reflexes by 43.0 to 200 mg/kg. of animal body weight i.p. of the test compound. 2) by their ability to produce docility in behavior tests in mice given 20.0 to 200 mg/kg. of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); 3) by their ability to antagonize clonic convulsions and death in mice given about 28.0 to 250 mg/kg. of the test compound followed immediately by 50 mg/kg. i.p. of N-sulfamoylazepine; and 4) by scoring for loss of righting reflex according to the method of Reed-Muench (American Journal of Hygiene, 27: 493-497), in which mice are administered 12.5 mg/kg. i.p. Thioridazine, immediately after which the test compound is administered at dosages of 65.0 to 100 mg/kg. in a volume of 0.1 ml/10 g. body weight. Sixty minutes after dosing, the mice are scored for loss of righting reflex.

The sleep inducing effective dosage of the compounds of formula (I) will vary depending on the particular compound employed. However, in general, satisfactory results are obtained when the compounds are administered orally at a daily dosage of from about 1.0 milligram to about 150 milligrams per kilogram of animal body weight, typically given in a single dose at bedtime. For most large mammals, the total daily dosage is from about 150 to 1000 milligrams, preferably at bedtime and dosage forms suitable for internal administration comprise from about 37.5 to about 500 milligrams of the compound in admixture with a solid or liquid pharmaceutical carrier or diluent.

For minor tranquilizer use in the treatment of anxiety and tension, the effective dosage will vary depending on the particular compound employed. However, in general, satisfactory results are obtained when the compounds are administered orally at a daily dosage of from about 1.0 milligrams to about 150 milligrams per kilogram of animal body weight, typically given in divided doses two to four times per day. For most large mammals, the total daily dosage is from about 50 to about 1000 milligrams, and dosage forms suitable for internal administration comprise from about 12.5 to about 500 milligrams of the compound in admixture with a solid or a liquid pharmaceutical carrier or diluent.

For the uses mentioned above, the compounds may be administered orally in such forms as tablets, capsules, elixirs, suspensions and the like or parenterally in the form of an injectable solution or suspensions. The dosage will vary depending upon the mode of administration utilized and the compound employed.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers in divided doses two to four times per day.

| Ingredients | Weight (mg.) tablet | capsule |
|---|---|---|
| o-(5-phenyl-3-isoxazolyl)-N-methyl benzamide | 200 | 200 |
| tragacanth | 10 | — |
| lactose | 247.5 | 300 |
| corn starch | 25 | — |
| talcum | 15 | — |
| magnesium stearate | 2.5 | — |
| TOTAL | 500 mg. | 500 mg. |

EXAMPLE 1

α-bromo-o-(5-phenyl-3-isoxazolyl)-toluene

A mixture of 37.5 g. (0.16 mole) 5-phenyl-3-o-ttolyl-isoxazole, 31.3 g. (0.176 mole) N-bromosuccinimide, 500 mg. benzoylperoxide and 400 ml. carbon tetrachloride is refluxed for 5 hours. The mixture is cooled and filtered and the solid washed with carbon tetrachloride and the carbon tetrachloride filtrate is washed with water, dried over anhydrous magnesium sulfate, filtered and evaporated in vacuo. The resulting solid is triturated with petroleum ether to give α-bromo-o-(5-phenyl-3-isoxazolyl)toluene; m.p. 68° to 72° C.

Following the above procedure and using in place of 5-phenyl-3-o-tolyl-isoxazole an equivalent amount of (a) 5-(p-chlorophenyl)-3-o-tolyl-isoxazole,
(b) 5-(p-fluorophenyl)-3-o-tolyl-isoxazole,
(c) 5-(p-anisyl)-3-o-tolyl-isoxazole or
(d) 5-(m-trifluoromethylphenyl)-3-o-tolyl-isoxazole there is obtained (a) α-bromo-o-(5-p-chlorophenyl-3-isoxazolyl)toluene,
(b) α-bromo-o-(5-p-fluorophenyl-3-isoxazolyl) toluene,
(c) α-bromo-o-(5-p-anisyl-3-isoxazolyl)toluene, or
(d) α-bromo-o-(5-m-trifluoromethylphenyl-3-isoxazolyl)toluene, respectively.

EXAMPLE 2 o-(5-phenyl-3-isoxazolyl)benzyl acetate

A mixture of 12.5 g. potassium acetate (0.128 mole), 20.1 g. (0.064 mole) α-bromo-o-(5-phenyl-3-isoxazolyl)-toluene and 200 ml. acetic acid is refluxed for 22 hours. The mixture is cooled and the acetic acid evaporated in vacuo. The residue is distilled on high vacuum and the fraction distilling at 140°–150° C. (0.25 mm) is collected and then crystallized from peteroleum ether containing a small amount of ether to give o-(5-phenyl-3-isoxazolyl)benzyl acetate; m.p. 50° to 62° C.

Following the above procedure and using in place of α-bromo-o-(5-phenyl-3-isoxazolyl)toluene an equivalent amount of (a) α-bromo-o-(5-p-chlorophenyl-3-isoxazolyl) toluene,
(b) α-bromo-o-(5-p-fluorophenyl-3-isoxazolyl) toluene,
(c) α-bromo-o-(5-p-anisyl-3-isoxazolyl)toluene, or
(d) α-bromo-o-(5-m-trifluoromethylphenyl-3-isoxazolyl)toluene there is obtained (a) o-(5-p-chlorophenyl-3-isoxazolyl)benzyl acetate,
(b) o-(5-p-fluorophenyl-3-isoxazolyl)benzyl acetate,
(c) o-(5-p-anisyl-3-isoxazolyl)benzyl acetate, or
(d) o-(5-m-trifluoromethylphenyl-3-isoxazolyl) benzyl acetate, respectively.

EXAMPLE 3 o-(5-phenyl-3-isoxazolyl)benzyl alcohol

A mixture of o-(5-phenyl-3-isoxazolyl)benzyl acetate, 35.2 ml. (0.352 mole) of 1 N sodium hydroxide solution and 95 ml. of ethanol is stirred for 4 days at room temperature. The ethanol is removed in vacuo and the aqueous material extracted with methylene chloride. The methylene chloride is washed with water, dried over anhydrous magnesium sulfate, filtered and evaporated in vacuo. The residue is crystallized from ether/petroleum ether to give o-(5-phenyl-3-isoxazolyl) benzyl alcohol; m.p. 68° to 70° C.

Following the above procedure and using in place of o-(5-phenyl-3-isoxazolyl)benzylacetate an equivalent amount of (a) o-(5-p-chlorophenyl-3-isoxazolyl)benzyl acetate,
(b) o-(5-fluorophenyl-3-isoxazolyl)benzyl acetate,
(c) o-(5-p-anisyl-3-isoxazolyl)benzyl acetate, or
(d) o-(5-m-trifluoromethylphenyl-3-isoxazolyl) benzyl acetate there is obtained (a) o-(5-p-chlorophenyl-3-isoxazolyl)benzyl alcohol,
(b) o-(5-p-fluorophenyl-3-isoxazolyl)benzyl alcohol,
(c) o-(5-p-anisyl-3-isoxazolyl)benzyl alcohol, or
(d) o-(5-m-trifluoromethylphenyl-3-isoxazolyl) benzyl alcohol, respectively.

EXAMPLE 4 o-(5-phenyl-3-isoxazolyl)benzoic acid

A mixture of 6.3 g. (0.025 mole) o-(5-phenyl-3-isoxazolyl)benzyl alcohol in 125 ml. acetone is added dropwise at room temperature to 50 ml. (0.1 mole) of a reagent prepared by dissolving 100 g. (1.0 mole) chromium trioxide in 160 g. of concentrated sulfuric acid and diluting with water to form a 500 ml. solution. The mixture is stirred for 3 hours at room temperature and then filtered. The acetone is evaporated in vacuo and the residue partitioned between ether and water. The resulting layers are separated and the ether washed with water, dried over anhydrous magnesium sulfate, filtered and evaporated in vacuo. The resulting solid is triturated with cold ether and filtered to give o-(5-phenyl-3-isoxazolyl) benzoic acid; m.p. 144.5° to 146.5° C.

Following the above procedure and using in place of o-(5-phenyl-3-isoxazolyl)benzyl alcohol an equivalent amount of (a) o-(5-p-chlorophenyl-3-isoxazolyl)benzyl alcohol,
(b) o-(5-p-fluorophenyl-3-isoxazolyl)benzyl alcohol,
(c) o-(5-p-anisyl-3-isoxazolyl)benzyl alcohol, or
(d) o-(5-m-trifluoromethylphenyl-3-isoxazolyl) benzyl alcohol there is obtained (a) o-(5-p-chlorophenyl-3-isoxazolyl)benzoic acid,
(b) o-(5-p-fluorophenyl-3-isoxazolyl)benzoic acid,
(c) o-(5-p-anisyl-3-isoxazolyl)benzoic acid, or
(d) o-(5-m-trifluoromethylphenyl-3-isoxazolyl) benzoic acid, respectively.

EXAMPLE 5 o-(5-phenyl-3-isoxazolyl)-N-methyl benzamide

A mixture of 4.2 g. (0.016 mole) o-(5-phenyl-3-isoxazolyl)benzoic acid and 35 ml. thionyl chloride is refluxed for 3 hours. The mixture is then cooled, and the thionyl chloride removed in vacuo. The resulting residue is twice treated with benzene and the solvent evaporated to obtain the corresponding benzoic acid chloride. The benzoic acid chloride is then dissolved in ether and added in a drop-wise manner to 75 ml. 40% aqueous methylamine at 0° to 10° C. The mixture is stirred for 18 hours and then filtered. The resulting solid is recrystallized from ethanol to give o-(5-phenyl-3-isoxazolyl)-N-methyl benzamide; m.p. 159° to 160° C.

Following the above procedure and using in place of o-(5-phenyl-3-isoxazolyl)benzoic acid an equivalent amount of (a) o-(5-p-chlorophenyl-3-isoxazolyl)benzoic acid,
(b) o-(5-p-fluorophenyl-3-isoxazolyl)benzoic acid,
(c) o-(5-p-anisyl-3-isoxazolyl)benzoic acid, or
(d) o-(5-m-trifluoromethylphenyl-3:isoxazolyl) benzoic acid there is obtained (a) o-(5-p-chlorophenyl-3-isoxazolyl)-N-methyl benzamide,
(b) o-(5-p-fluorophenyl-3-isoxazolyl)-N-methyl benzamide,
(c) o-(5-p-anisyl-3-isoxazolyl)-N-methyl benzamide, or
(d) o-(5-m-trifluoromethylphenyl-3-isoxazolyl)-N-methyl benzamide, respectively.

The o-(5-phenyl-3-isoxazolyl)-N-methyl benzamide of this example is an effective minor tranquilizer when orally administered to an animal in need of said treatment at a dosage of 100 mg. two to four times per day. The compound of this example is also effective as a sleep inducer when orally administered to an animal in need of said treatment at a dosage of 200 mg. just before bedtime.

What is claimed is:

1. A compound of the formula

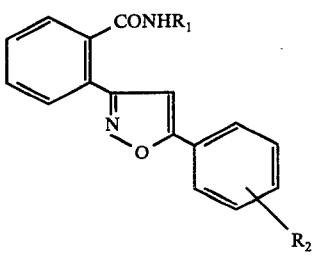

where
R$_1$ is straight chain lower alkyl, and
R$_2$ is hydrogen, fluoro or chloro, lower alkoxy or trifluoromethyl.

2. A compound of the formula

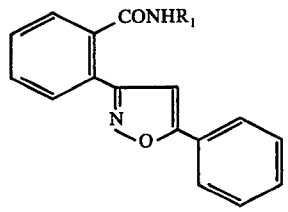

where R$_1$ is as defined in claim 1.

3. A compound of the formula

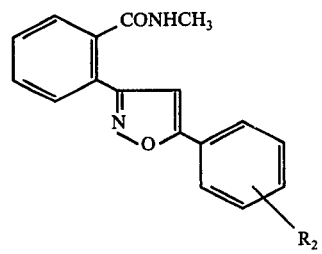

where R$_2$ is as defined in claim 1.

4. The compound of claim 1 which is o-(5-phenyl-3-isoxazolyl)-N-methyl benzamide.

5. The method of treating insomnia which comprises administering to a mammal in need of said treatment an effective amount of a compound according to claim 1.

6. The method of treating anxiety, which comprises administering to a mammal in need of said treatment an effective amount of a compound according to claim 1.

7. A pharmaceutical composition for use in the treatment of insomnia or anxiety which comprises a therapeutically effective amount of a compound of claim 1 and a pharmaceutically acceptable carrier therefor.

* * * * *